(12) United States Patent
Faughey et al.

(10) Patent No.: US 6,394,317 B1
(45) Date of Patent: May 28, 2002

(54) PUMP DISPENSER

(75) Inventors: Michael Faughey, Harleyville, PA (US); John Lonczak, Newburgh, NY (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/693,230

(22) Filed: Oct. 20, 2000

Related U.S. Application Data (62) Division of application No. 09/387,943, filed on Sep. 1, 1999, now Pat. No. 6,164,498.

(51) Int. Cl.⁷ .................................................. G01F 11/00
(52) U.S. Cl. ............... 222/309; 222/153.13; 222/321.6; 222/48; 604/211
(58) Field of Search ............................. 222/309, 321.6, 222/153.13, 48; 128/200.23; 604/211

(56) References Cited

U.S. PATENT DOCUMENTS

| | | |
|---|---|---|
| 1,917,672 A | 7/1933 | Stewart |
| 2,968,423 A | 1/1961 | Mahler et al. |
| 2,989,215 A | 6/1961 | Willingham |
| 3,097,763 A | 7/1963 | Aluotto |
| 3,101,751 A | 8/1963 | Ballin |
| 3,141,579 A | 7/1964 | Medlock |
| 3,233,797 A | 2/1966 | Conry |
| 3,321,113 A | 5/1967 | Conry |
| 3,458,090 A | 7/1969 | Scoggin, Jr. |
| 3,492,876 A | 2/1970 | Bull et al. |
| 3,543,964 A | 12/1970 | Schlossmacher |
| 3,556,353 A | 1/1971 | Echols |
| 3,653,556 A | 4/1972 | Moran et al. |
| 3,863,807 A | 2/1975 | Shapiro et al. |
| 4,143,794 A | 3/1979 | Stratford et al. |
| 4,143,797 A | 3/1979 | Reed |
| 4,185,755 A | 1/1980 | Sachs et al. |
| 4,211,346 A | 7/1980 | Mehra et al. |
| 4,243,157 A | 1/1981 | Rettberg |
| 4,407,435 A | 10/1983 | Harmon |
| 4,433,799 A | 2/1984 | Corsette |
| 4,445,626 A | 5/1984 | Steffen et al. |
| 4,454,964 A | 6/1984 | Sacher |
| 4,456,152 A | 6/1984 | Young et al. |
| 4,474,312 A | 10/1984 | Donoghue |
| 4,526,294 A | 7/1985 | Hirschmann et al. |
| 4,607,762 A | 8/1986 | Zulauf et al. |
| 4,747,521 A | 5/1988 | Saffron |
| 4,871,092 A | 10/1989 | Maerte |
| 4,936,490 A | 6/1990 | Battegazzore |
| 4,944,429 A | 7/1990 | Bishop et al. |
| 5,000,353 A | 3/1991 | Kostanecki et al. |
| 5,007,757 A | 4/1991 | Iizuka |
| 5,044,521 A | 9/1991 | Peckels |
| 5,050,782 A | 9/1991 | Cheng |
| 5,067,638 A | 11/1991 | Bavaveas |
| 5,119,971 A | 6/1992 | Reyman |
| 5,127,553 A | 7/1992 | Weinstein |
| 5,228,586 A | 7/1993 | Fuchs |
| 5,251,792 A | 10/1993 | Sheen |
| 5,261,569 A | 11/1993 | Sandwell |
| 5,330,081 A | 7/1994 | Davenport |
| 5,363,991 A | 11/1994 | Reyman |
| 5,363,992 A | 11/1994 | Meshberg |
| 5,411,181 A | 5/1995 | Knickerbocker |

Primary Examiner—Philppe Derakshani
Assistant Examiner—Thach H Bui
(74) Attorney, Agent, or Firm—Michele G. Mangini; Joseph F. Leightner (57) ABSTRACT

The present invention provides a container which provides a measured dosage of the contents of the container when pressure is applied to the top of the container. When not in use, the container additionally contains a locking means such that the contents of the container cannot be dispensed without repositioning the locking means to the open position.

9 Claims, 8 Drawing Sheets

PUMP DISPENSER

CROSS-REFERENCE TO RELATED APPLICATION

This Application is a divisional application of U.S. application No. 09/387,943 filed on Sep. 1, 1999, now U.S. Pat. No. 6,164,498 which is incoporated reference in its entirety herein.

FIELD OF THE INVENTION

The present invention relates to a pump dispenser for liquids, more specifically to a pump dispenser which is designed to deliver a measured dosage of a liquid which contains a pharmaceutical ingredient.

BACKGROUND OF THE INVENTION

Liquid dispensing devices are used in various purposes for domestic, industrial and scientific environments. A common design employs a plunger in a barrel where the liquid is forced out of a nozzle connected to a plunger as the plunger is depressed. A recent development is disclosed in U.S. Pat. No. 5,050,782 in which the plunger is selectively limited in its depression thereby providing a predetermined amount of liquid. While this design is capable of delivering a measured dosage of liquid, the devise is not well suited for the delivery of pharmaceutical ingredients. This shortcoming is particularly apparent in the dosage of pharmaceutical ingredients which can not be sold without childproof protection. Those with skill in the art appreciate the need to provide accurate delivery of pharmaceutical ingredients while also preventing an accidental overdosing by the children who gain access to a dispenser.

SUMMARY OF THE INVENTION

1. The present invention provides a bottle for dispensing a product, said bottle comprising:
   a. an enclosed container for storing said product, said container having a top, a bottom and a longitudinal axis therebetween, said container having an opening at said top;
   b. a dispenser having a bottom attached to said top of said container, and a top having an orifice therethrough in communication with said opening for dispensing said product, said dispenser is movable in said longitudinal direction, such that when said dispenser is moved in a downward direction, towards said bottom, product is dispensed from said container through said orifice, said dispenser comprising;
      i. a substantially hollow cylindrical external collar fitted about said opening of said container, said collar having a flange extending from an internal surface thereof towards an interior thereof;
      ii. an internal collar disposed within said interior of said external collar such that said internal collar can rotate and move longitudinally relative to said external collar, said internal collar having a rectangular boss and an L-shape boss spaced apart from one another and extending towards said exterior collar, said internal collar is disposed within said external collar such that it is movable between a locked position, wherein said flange is disposed on top of said L-shape boss thereby preventing downward movement of said dispenser, and an open position wherein said flange is between a space between said L-shape boss and said rectangular boss.

2. In a second embodiment of the invention a bottle for dispensing a product, said bottle comprising:
   a. an enclosed container for storing said product, said container having an opening at a top thereof; and
   b. a dispenser movably attached to said top of said container such that when said dispenser is moved downward, towards said container, product is dispensed therefrom, said dispenser comprising;
      i. an external collar fitted about said opening of said container, said collar having a flange extending inwardly from an internal surface thereof; and
      ii. an internal collar movably disposed within an interior of said external collar, said internal collar having a boss extending outwardly therefrom, said dispenser is movable between an open position, and a locked position, wherein said flange engages said boss such that said dispenser prevented from moving downward.

DETAILED DESCRIPTION OF THE INVENTION

The present invention provides a means for providing a mechanism for the adjusting the volumetric delivery of the dispenser by limiting the travel of the stroke of the dispenser. The volumetric delivery is limited by the rotational adjustment of the dispenser through a plurality of channels set forth in the outer collar. In addition to the volumetric delivery of the liquid, the container additionally contains separate locking means which prevent the downward travel of the dispenser unless the locking means is in the open position. The locking means provides a child resistant feature which provides that the container is rendered inoperable when in the closed position.

Figure 1:
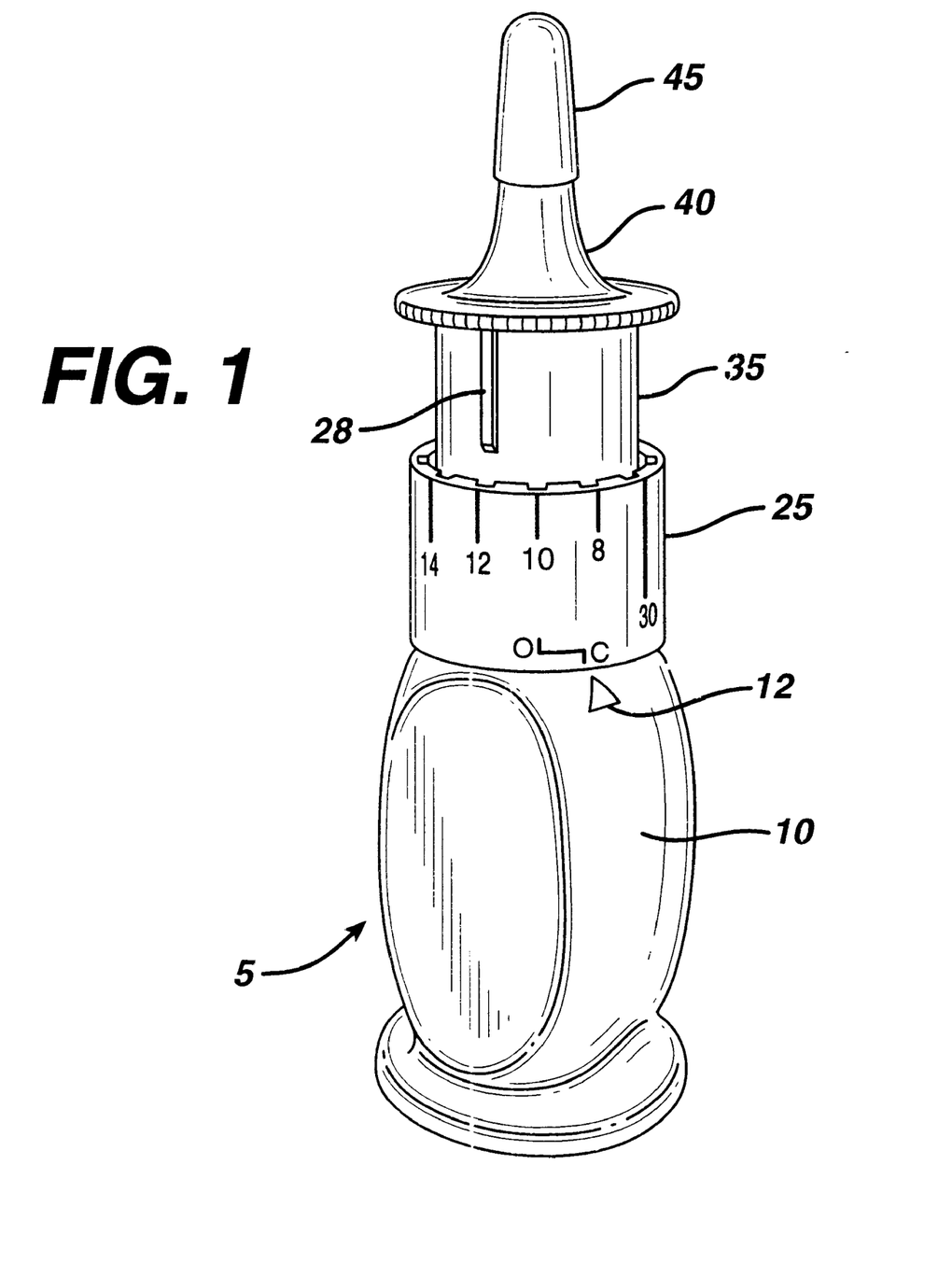
FIG. 1 is a perspective view of the container with the position indicator in the closed position.

FIG. 1 depicts the bottle 5 as the consumer would initially purchase it. The container 10 holds the liquid, and the position indicator 12 is in the closed (C) position. The indicator dosage collar 25 with a plurality of dosages is visible and the dosage indicator 28 on the internal collar 35 is positioned at the numeral 12. The dispenser 40 and cap 45 are also visible.

Figures 2, 3:
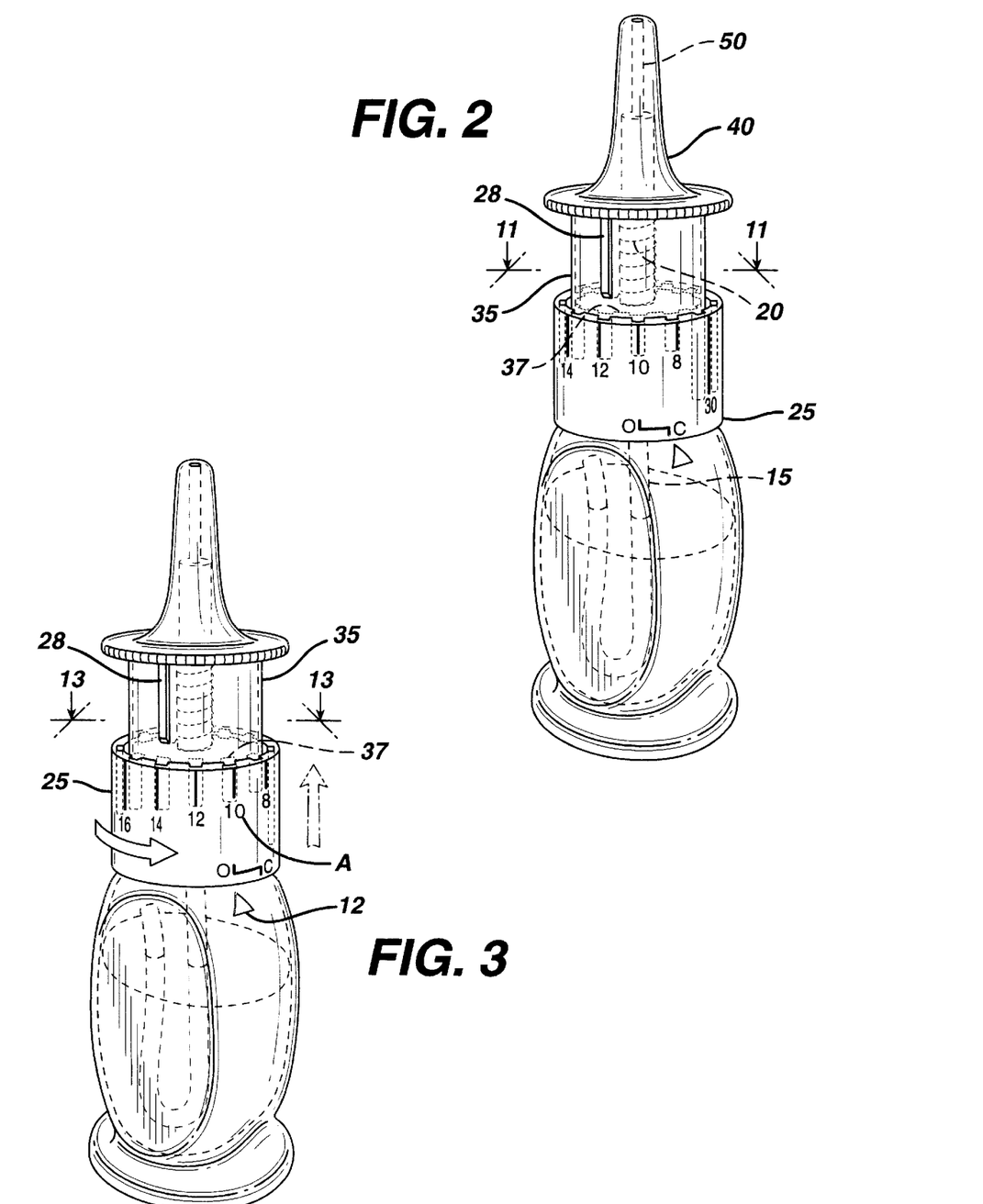
FIG. 2 is a perspective view of the container with the position indicator in the closed position and the cap removed.
FIG. 3 is a perspective view of the container rotated with the position indicator shown in the unlocked position.

FIG. 2 provides a perspective view of the container with the dispensing tube 15 visible. The position indicator 12 is in the closed position. In a preferred embodiment the dispensing tube is in a U-shape as depicted herein, although those with skill in the art will appreciate that other shapes for the dispensing tube, such as straight, angled, L shape and the like, can be employed without departing from the scope of the present invention. The dispersing tube 20 maintains constant pressure on the dispenser 40. The dispensing tube extension 50 is depicted by the dashed lines. The plurality of channels in the internal collar 37 are also visible.

FIG. 3 depicts the lifting and rotation of the indicator dosage collar 25 as depicted by the arrow, which when in alignment indicates that the position indicator 12 is now in the open (O) position.

Figure 4:
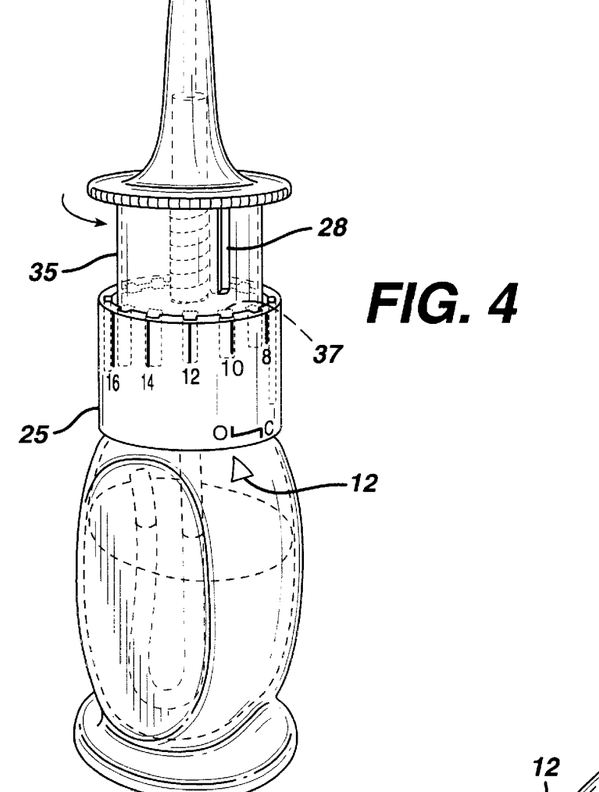
FIG. 4 is a perspective view of the container wherein the dosage indicator is been rotated to the desired dosage level suitable for a child weighing 10 pounds.

FIG. 4 provides the selection of the proper dosage by the rotation of the internal collar in the direction of the arrow. The dosage indicator 28 is now at the numeral 10 (A).

Figure 5:
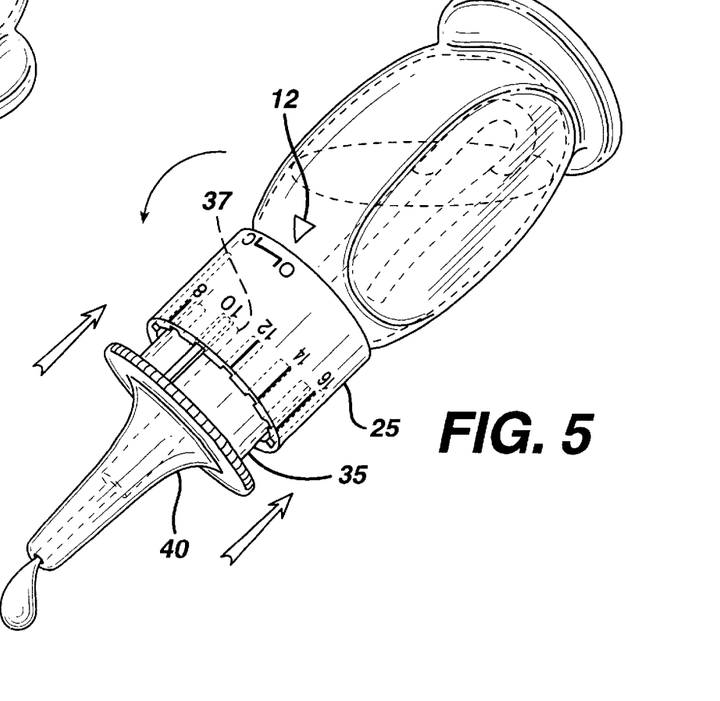
FIG. 5 is a perspective view showing the container in an inverted position with pressure being applied to the dispenser providing a measured dosage of the contents of the container.

FIG. 5 depicts the how the container of the present invention is intended to be used. The container and its contents are inverted. With the position indicator 12 in the open position (O), pressure is applied to the dispenser 40 which causes the dispenser to travel the length of the channel in the internal collar 37 to which the indicator dosage collar is set. This predetermined level of liquid is then dispensed from the container to the consumer.

Figure 6:
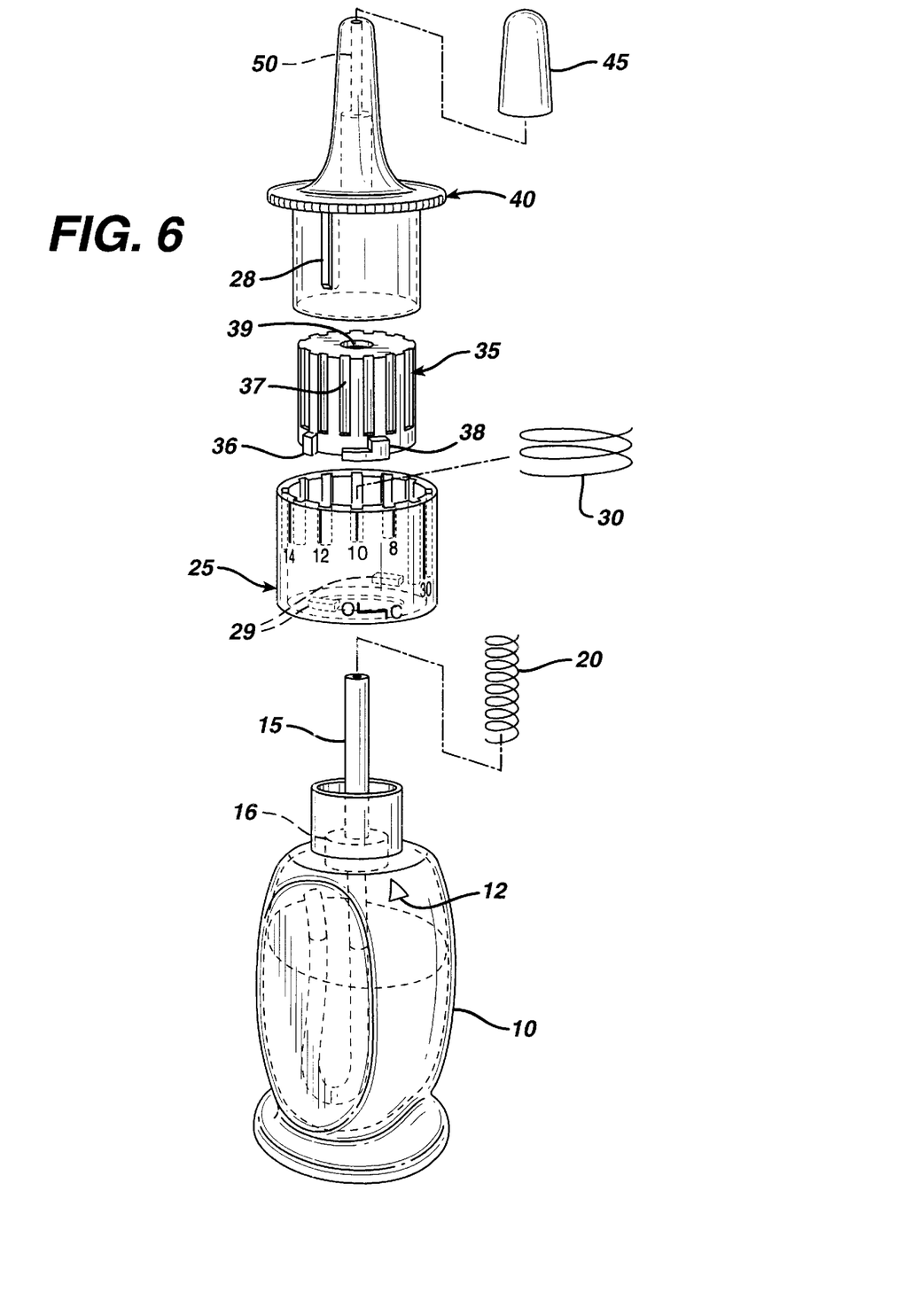
FIG. 6 is an exploded perspective view the container depicting the relationship of various elements of the container.

FIG. 6 is an exploded view of the elements of the container design. The container 10 and position indicator 12 are shown. The dispensing tube 15 is apparent with a gasket means 16 separating the contents of the container from the upper regions of the bottle. The indicator dosage collar 25 and the indicator dosage flanges, also referred to as lugs 29, and dispensing tube spring 20 are shown. The collar spring 30 provides tension on the internal collar 35, and the L-shape boss 38 and rectangular boss 36 on the internal collar are also shown. The internal collar aperture 39 in which the dispensing tube passes through is also apparent. The dispenser 40 with the dosage indicator 28 is visible. The dispensing tip extension 50 extending beyond the dispensing tube is shown by the dotted line. A cap 45 is provided for hygiene and to prevent spills.

Figure 7:
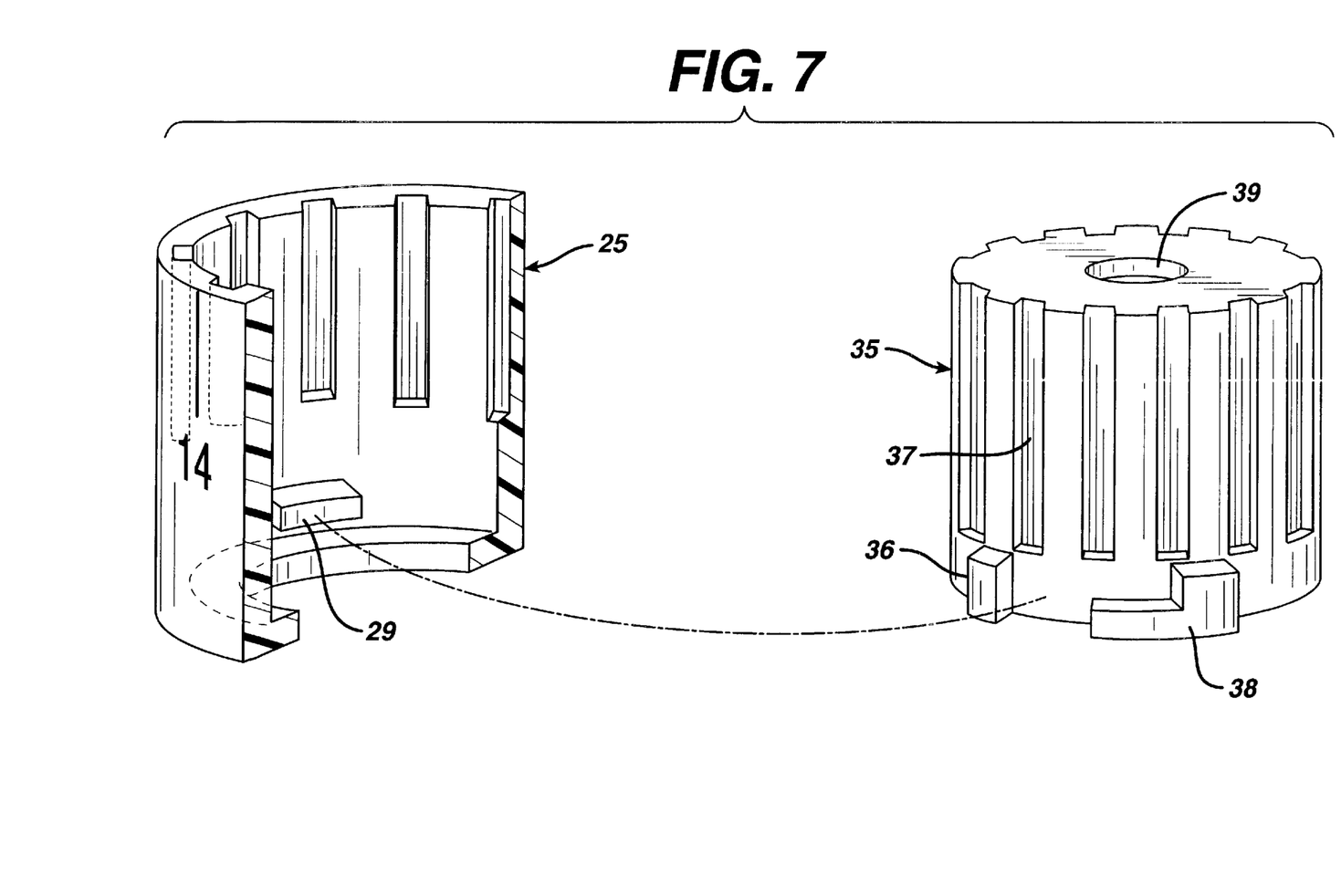
FIG. 7 is a perspective view in partial section of the internal collar, showing the interaction of the lugs which constitute the child resistant feature.
Figure 8:
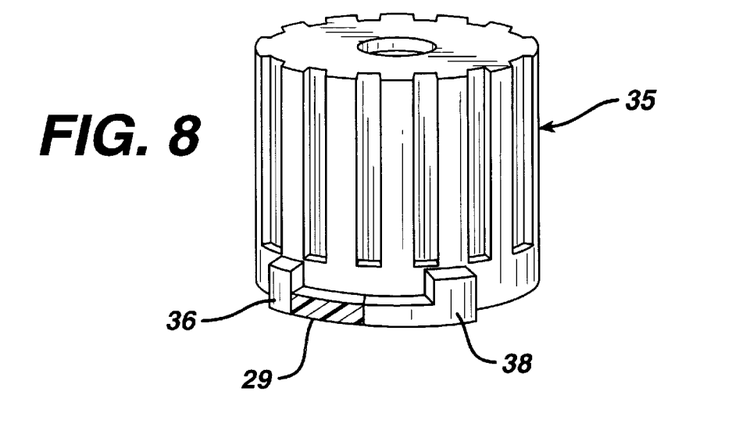
FIGS. 8, 9 and 10 are perspective views showing the internal collar depicting the relationship of the flanges and bosses in a first locked position as set forth in FIG. 8; an intermediate position in FIG. 9; and in an unlocked position in FIG. 10.

FIG. 7 depicts a cut away view of the flanges 29, the L-shape boss 38 and the rectangular boss 36 on the inner collar 35. In FIG. 8 the flanges, including indicator dosage flange 29, the L-shape boss 38 and the rectangular boss 36 are in the locked position. This prevents the dispenser from being depressed and the contents of the container from being dispensed by ensuring the misalignment of the dosage indicator 28 with the longitudinal slots on the internal collar 35.

Figure 9:
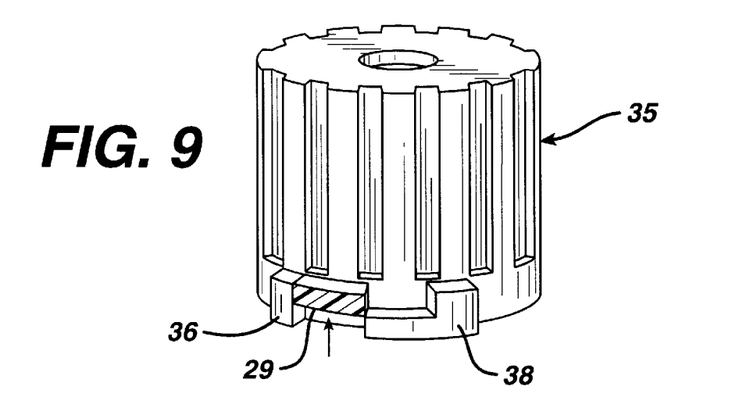
Figure 10:
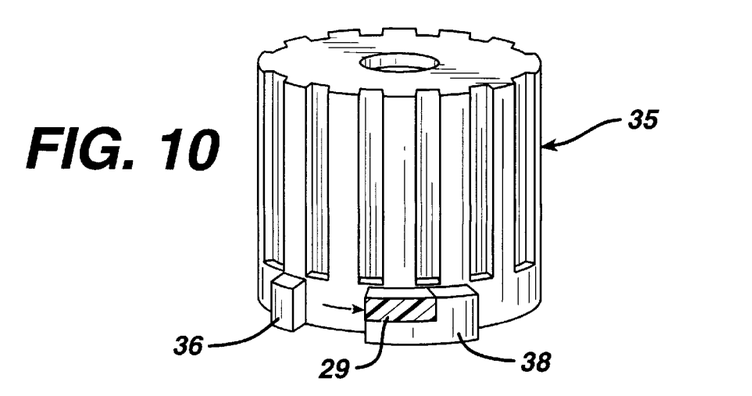

FIG. 9 depicts an intermediate position and an unlocked position in FIG. 10. The numerals in FIGS. 9 and 10 are the same elements as set forth in FIG. 8.

Figure 11:
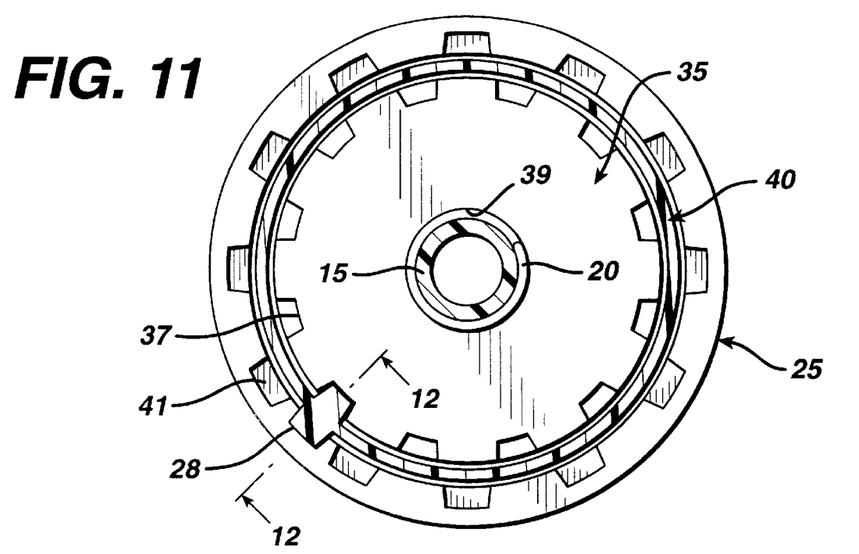
FIG. 11 is a cross-sectional view of the internal collar and dispenser taken along section line 11—11 of FIG. 2 shown in a first locked position.

FIG. 11 depicts the arrangement of the internal collar 35 and indicator dosage collar 25 in a locked position. Because the indicator dosage collar and inner collars are not in proper alignment, it is not possible for the dispenser 40 to be depressed into anyone of the axial channels of the inner collar. The internal collar aperture 39 is visible as well as the dip tube extension 50.

Figure 12:
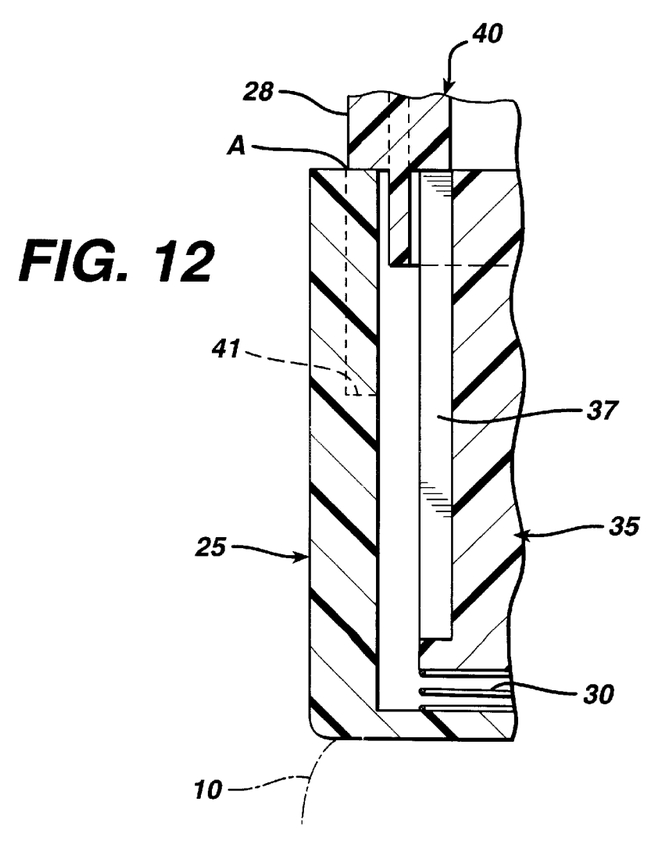
FIG. 12 is a partial cross-sectional view of the internal collar and dispenser taken along section line 12—12 of FIG. 11.

FIG. 12 is a side depiction of the view taken along line. 12—12. The internal collar 35 is not aligned with the channels of the indicator dosage collar 25, thereby making it impossible to depress the dispenser. The dispenser 40 is prevented from being depressed because it is locked by the indicator dosage collar at point A. The collar spring 30 is visible. The axial channel 41 is depicted by the dashed line.

Figure 13:
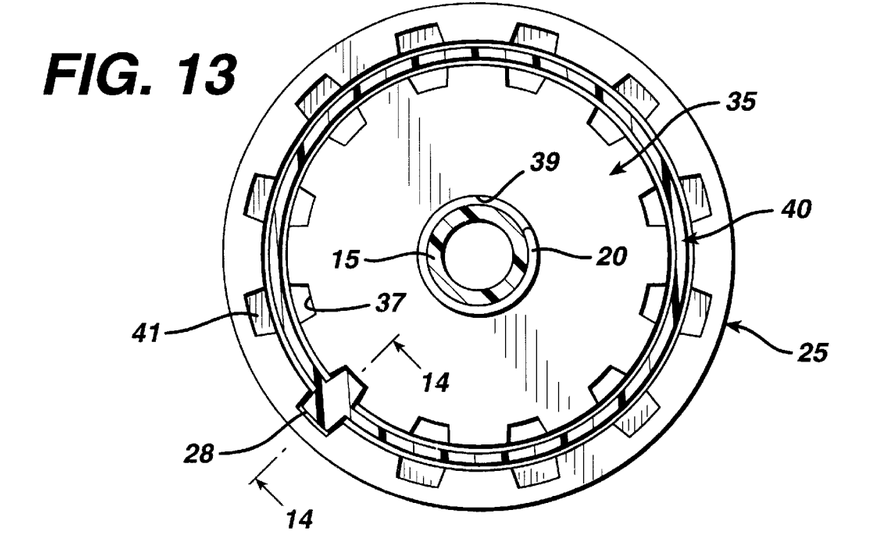
FIG. 13 is a cross-sectional view similar to FIG. 11 taken along section line 13—13 of FIG. 3 but showing the dispenser in a second unlocked position.

FIG. 13 depicts the arrangement of the inner collar 35, the internal collar aperture 39 and indicator collar 40 in an open position, capable of dispensing a measured dosage of liquid from the container. The other elements are the same as depicted in FIG. 11.

Figure 14:
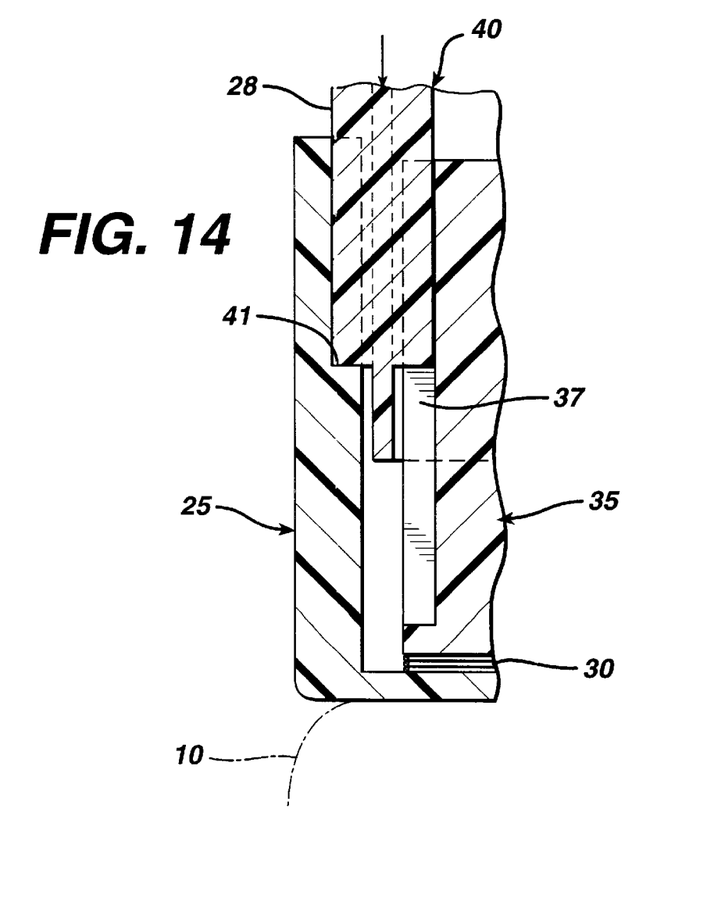
FIG. 14 is a partial cross-sectional view of the dispenser and internal collar taken along section line 14—14 of FIG. 13.

FIG. 14 depicts the dispenser having been depressed in the direction of the arrow. The inner collar will be permitted to travel in the channel of the indicator dosage collar 25 until it comes to rest on the axial channel shoulder 41. Upon release of applied pressure, the inner collar 35 will return to its resting position and can incorporate designs which re-engage the child resistant feature into the locked position.

The present invention provides a novel and particularly convenient mechanism for adjusting the length of the downstroke of plunger element. By such adjustment of the downstroke length by the proper selection of the axial channel, the volumetric delivery of the liquid dispensing device can be adjusted so that at the dispenser provides for the delivery of premeasured volumes of liquid when the dispenser 40 is in its raised position, projection will be received in annular channel so that the dispenser will be able to freely rotate relative to the indicator dosage collar 25. In this way, the dosage indicator may be brought into alignment with any one of the channels, each of which have different lengths. Once the dosage indicator is brought into such alignment, the dispenser may be depressed downward relative to container and the container inverted so that liquid can be dispensed in a conventional manner. The length of downward travel, however, is limited by the length of the particular axial channel which has been selected. The amount of volume delivered by the dispenser will thus be a function of the length of the channel, which has been selected. An axial channel which is one-half the length of the dispenser will generally deliver about one-half of the total volume which is held within the dispenser. Correspondingly longer and shorter strokes will deliver correspondingly larger and smaller liquid volumes.

In addition to the position indicator, another child resistant feature can be incorporated into the cap. The term child-resistant is understood to those with skill in the packaging arts. These packages require a level of cognitive skills such that most children can not gain access to the contents of the dispenser. Numerous child-resistant means are known in the art, including but not limited to alignment of tabs or flaps to open the container top, a plurality of grooves and channels which require the user to push down on the container top to engage the grooves. These techniques are disclosed in U.S. Pat. Nos. 3,795,338, 3,857,505, the contents incorporated by reference as set forth in their entirety. The preferred embodiment in the present invention are the use of tabs which must be aligned before the cap can be removed.

The present invention is particularly well suited to dispense solutions which contain a pharmaceutical agent. The present invention can be used to dispense any liquids, including solutions, dispersions and suspensions. Suitable pharmaceutically acceptable dispersants and suspending agents are well known in the art, see for example, *Remington Pharmaceutical Sciences*, 15th Edition. Techniques for making such suspensions and dispersions are known to those with skill in the art, see for example, U.S. Pat. Nos. 5,272,137; 5,374,659; 5,409,907; 5,621,005; and 5,658,919; the contents of which are incorporated by reference.

The present invention may be used to deliver many active medicaments that are well known in the art. U.S. Pat. No. 4,929,508 provides a suitable list of such medicaments and the relevant portions of the patent are hereby incorporated by reference. The form of the medicaments are not critical in the invention so long as they may be incorporated into a liquid. The original form of the pharmaceutically active ingredient before incorporation into the liquid may be solids, liquids, powders, pellets and the like.

Especially preferred medicaments to be delivered by the present invention include ibuprofen, acetaminophen, aspirin, pseudoephedrine, pseudoephedrine hydrochloride, chlorpheniramine maleate, dextromethorphan hydrobromide, diphenhydramine, loratadine, phenylpropanolamine and diphenydramine hydrochloride.

Commonly known pharmaceutically acceptable additives for orally-administered drugs such as sweeteners, colorings, flavoring agents, buffering agents and the like may be included in the formulations. Suitable sweeteners include sugar, sorbitol, saccharin, mannitol, glucose, aspartame and the like. Flavoring agents include peppermint, spearmint cinnamon, bubble gum, vanilla and the like.

The container and the various parts are preferably made from plastic materials such as polyethylene, polyethylene terephthalate, polypropylene and the like. These plastics are preferred in that they are readily molded and formed as well as acceptable for handling liquids which contain pharmaceutically active materials. Other materials such as glass and metals may be incorporated into the present invention.

Although the foregoing invention has been described in detail for purposes of clarity of understanding, it will be obvious that certain modifications may be practiced within the scope of the appended claims.

We claim:

1. A bottle for dispensing a product, said bottle comprising:

an enclosed container for storing said product, said container having a top, a bottom and a longitudinal axis therebetween, said container having an opening at said top; a dispenser having a bottom attached to said top of said container, and a top having an orifice therethrough in communication with said opening for dispensing said product, said dispenser is movable in said longitudinal direction, such that when said dispenser is moved in a downward direction, towards said bottom, product is dispensed from said container through said orifice, said dispenser comprising;

a substantially hollow cylindrical external collar fitted about said opening of said container, said collar having a flange extending from an internal surface thereof towards an interior thereof;

an internal collar disposed within said interior of said external collar such that said internal collar can rotate and move longitudinally relative to said external collar, said internal collar having a rectangular boss and an L-shape boss spaced apart from one another and extending towards said exterior collar, said internal collar is disposed within said external collar such that it is movable between a locked position, wherein said flange is disposed on top of said L-shape boss thereby preventing downward movement of said dispenser, and an open position wherein said flange is between a space between said L-shape boss and said rectangular boss.

2. A bottle for dispensing a product, the bottle comprising:

a. an enclosed container for storing the product, the container having a top, a bottom, and a longitudinal axis therebetween, the container having an opening at the top;

b. a top having an orifice therethrough in communication with the opening for dispensing the product;

c. a dispenser having a bottom attached the top of the container, the dispenser is movable in the longitudinal direction such that when the dispenser is moved in a downward direction, towards the bottom, the product is dispensed from the container through the orifice, the dispenser comprising:

1) a substantially hollow cylindrical external collar fitted about the opening of the container, the collar having a flange extending from an internal surface thereof towards an interior thereof;

2) an internal collar disposed within the interior of the external collar such that the internal collar can rotate and move longitudinally relative to the external collar, the internal collar having a rectangular boss and an L-shape boss spaced apart from one another and extending towards the exterior collar, the internal collar is disposed within the external collar such that it is movable between a locked position, wherein the flange is disposed on top of the L-shape boss thereby preventing downward movement of the dispenser, and an open position wherein the flange is between a space between the L-shape boss an the rectangular boss;

3) a dosage indicator integral with said dispenser; and 4) at least one axial channel in said external collar, such that when the dispenser is moved downward towards the container, the dosage indicator is brought into alignment with the at least one axial channel and the product can be dispensed from the container upon inversion.

3. The bottle of claim 2 wherein the at least one axial channel is a plurality of channels of different lengths.

4. A bottle for dispensing a product, the bottle comprising:

a. an enclosed container for storing the product, the container having an opening at the top thereof;

b. a dispenser movably attached the top of the container such that when the dispenser is moved in a downward direction, towards the container, the product is dispensed therefrom, the dispenser comprising:

1) an external collar fitted about the opening of the container, the collar having a flange extending inwardly from an internal surface thereof;

2) an internal collar movably disposed within an interior of the external collar, the internal collar having a rectangular boss and an L-shape boss spaced apart from one another and extending outwardly therefrom, the dispenser is movable between an open position and a locked position, wherein the flange is in a relative position to the L-shape boss, thereby preventing downward movement of the dispenser;

3) a dosage indicator integral with said dispenser; and
4) at least one axial channel in said external collar, such that when the dispenser is moved downward towards the container, the dosage indicator is brought into alignment with the at least one axial channel and the product can be dispensed from the container upon inversion.

5. The bottle of claim 4 wherein the at least one axial channel is a plurality of channels of different lengths.

6. A bottle for dispensing a product, the bottle comprising:
a. an enclosed container for storing the product, the container having an opening at the top thereof;
b. a dispenser movably attached the top of the container such that when the dispenser is moved downward, towards the container, the product is dispensed therefrom, the dispenser comprising:
 1) an external collar fitted about the opening of the container, the collar having a flange extending inwardly from an internal surface thereof;
 2) an internal collar movably disposed within an interior of the external collar, the internal collar having a rectangular boss and an L-shape boss spaced apart from one another and extending outwardly therefrom, the dispenser is movable between an open position and a locked position, wherein the flange engages the L-shape boss such that the dispenser is prevented from moving downward;
 3) a dosage indicator integral with said dispenser; and
 4) at least one axial channel in said external collar, such that when the dispenser is moved downward towards the container, the dosage indicator is brought into alignment with the at least one axial channel and the product can be dispensed from the container upon inversion.

7. The bottle of claim 6 wherein the at least one axial channel is a plurality of channels of different lengths.

8. A bottle for dispensing a product, the bottle comprising:
a. an enclosed container for storing the product, the container having an opening at the top thereof;
b. a dispenser movably attached the top of the container such that when the dispenser is moved downward, towards the container, the product is dispensed therefrom, the dispenser comprising:
 1) an external collar fitted about the opening of the container, the collar having a flange extending inwardly from an internal surface thereof;
 2) an internal collar movably disposed within an interior of the external collar, the internal collar having a boss extending outwardly therefrom, the dispenser is movable between an open position and a locked position, wherein the flange engages the boss such that the dispenser is prevented from moving downward;
 3) a dosage indicator integral with said dispenser; and
 4) at least one axial channel in said external collar, such that when the dispenser is moved downward towards the container, the dosage indicator is brought into alignment with the at least one axial channel and the product can be dispensed from the container upon inversion.

9. The bottle of claim 8 wherein the at least one axial channel is a plurality of channels of different lengths.

* * * * *